United States Patent [19]

Nigam

[11] 4,333,474

[45] Jun. 8, 1982

[54] ULTRASONIC IMAGING SYSTEM

[75] Inventor: Anant K. Nigam, Plantation, Fla.

[73] Assignee: New York Institute of Technology, Old Westbury, N.Y.

[21] Appl. No.: 157,398

[22] Filed: Jun. 9, 1980

Related U.S. Application Data

[60] Continuation of Ser. No. 875,442, Feb. 6, 1978, Pat. No. 4,207,901, which is a division of Ser. No. 665,898, Mar. 11, 1976, Pat. No. 4,084,582.

[51] Int. Cl.³ .............................................. A61B 5/00
[52] U.S. Cl. .................................................... 128/660
[58] Field of Search .................. 128/24 A, 660–663, 128/618, 619, 620; 73/624, 628, 633, 641

[56] References Cited

U.S. PATENT DOCUMENTS

| 3,251,219 | 5/1966 | Hertz et al. | 128/661 |
| 3,765,403 | 10/1973 | Brenden | 128/660 |
| 3,815,409 | 6/1974 | Macovski | 73/620 |
| 3,821,891 | 7/1974 | Cullins et al. | 128/660 |
| 3,936,791 | 2/1976 | Kossoff | 128/660 |
| 4,117,446 | 9/1978 | Alais | 128/660 |

*Primary Examiner*—William E. Kamm
*Attorney, Agent, or Firm*—Martin Novack

[57] ABSTRACT

The invention is directed to an ultrasonic apparatus for imaging sections of a body, including a reflective scanner. Two transducers are employed, one for transmitting and the other for receiving. The transducer used for transmitting is mounted in conjunction with the reflective scanner, and is closer to the body being examined than is the transducer used for receiving ultrasound reflected from the body being examined.

7 Claims, 6 Drawing Figures

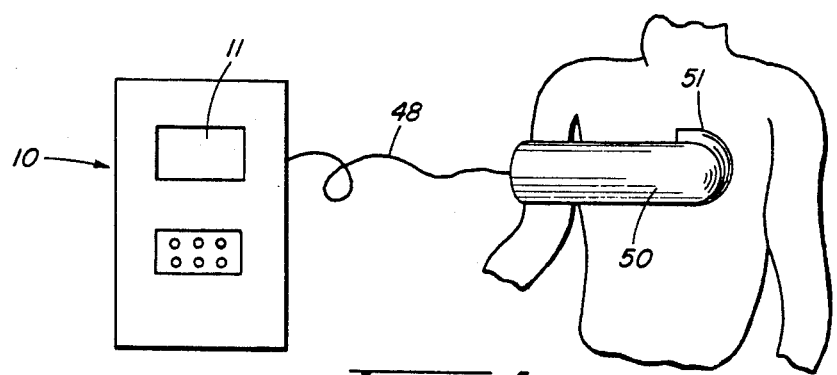
FIG. 1
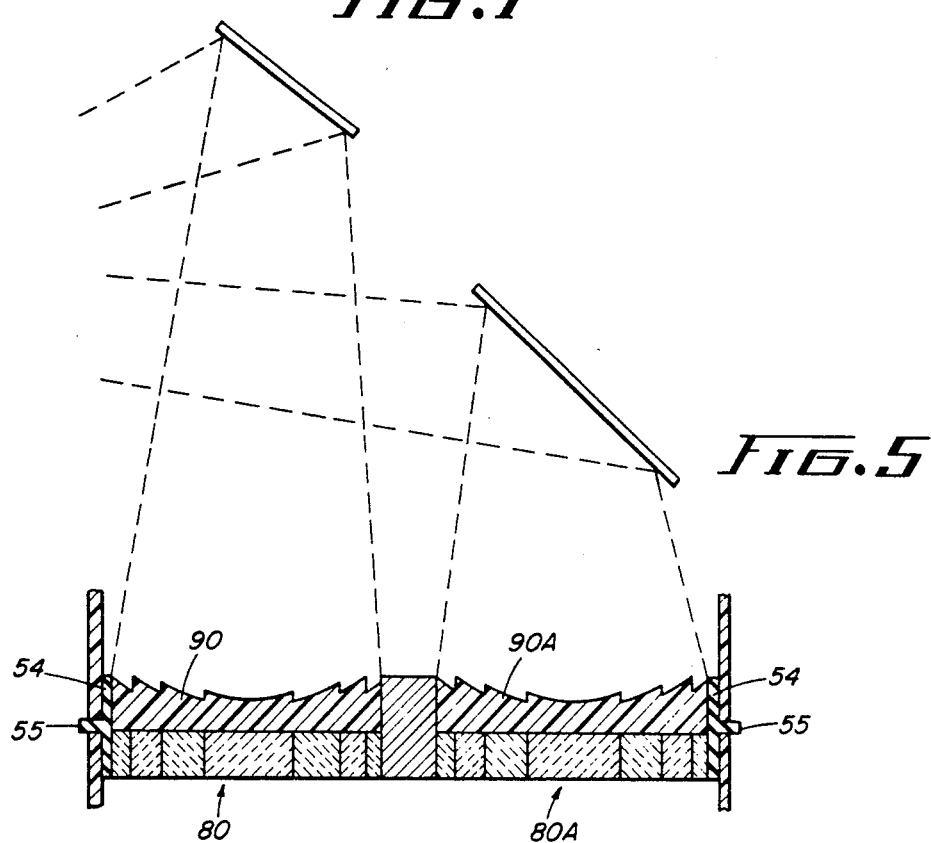
FIG. 5
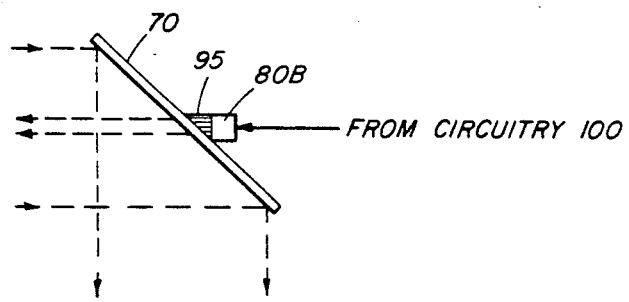

ULTRASONIC IMAGING SYSTEM

This is a continuation of application Ser. No. 875,442, filed Feb. 6, 1978, now U.S. Pat. No. 4,207,901, which is, in turn, a divisional of application Ser. No. 665,898 filed Mar. 11, 1976, now U.S. Pat. No. 4,084,582.

BACKGROUND OF THE INVENTION

This invention relates to ultrasonic systems and, more particularly, to apparatus for imaging sections of a body by transmitting ultrasonic energy into the body and determining the characteristics of the ultrasonic energy reflected therefrom.

During the past two decades ultrasonic techniques have become more prevalent in clinical diagnosis. Such techniques have been utilized for some time in the field of obstetrics, neurology and cardiology, and are becoming increasingly important in the visualization of subcutaneous blood vessels including imaging of smaller blood vessels.

Various fundamental factors have given rise to the increased use of ultrasonic techniques. Ultrasound differs from other forms of radiation in its interaction with living systems in that it has the nature of a mechanical wave. Accordingly, information is available from its use which is of a different nature than that obtained by other methods and it is found to be complementary to other diagnostic methods, such as those employing X-rays. Also, the risk of tissue damage using ultrasound appears to be much less than the apparent risk associated with ionizing radiations such as X-rays.

The majority of diagnostic techniques using ultrasound are based on the pulse-echo method wherein pulses of ultrasonic energy are periodically generated by a suitable piezoelectric transducer such as a lead zirconate-titanate ceramic. Each short pulse of ultrasonic energy is focused to a narrow beam which is transmitted into the patient's body wherein it eventually encounters interfaces between various different structures of the body. When there is a characteristic impedence mismatch at an interface, a portion of the ultrasonic energy is reflected at the boundary back toward the transducer. After generation of the pulse, the transducer operates in a "listening" mode wherein it converts received reflected energy or "echoes" from the body back into electrical signals. The time of arrival of these echoes depends on the ranges of the interfaces encountered and the propagation velocity of the ultrasound. Also, the amplitude of the echo is indicative of the reflection properties of the interface and, accordingly, of the nature of the characteristic structures forming the interface.

There are various ways in which the information in the received echoes can be usefully presented. In one common technique, the electrical signal representative of detected echoes are amplified and applied to the vertical deflection plates of a cathode ray display. The output of a time-base generator is applied to the horizontal deflection plates. Continuous repetition of the pulse/echo process in synchronism with the time-base signals produces a continuous display, called an "A-scan", in which time is proportional to range, and deflections in the vertical direction represent the presence of interfaces. The height of these vertical deflections is representative of echo strength.

Another common form of display is the so-called "B-scan" wherein the echo information is of a form more similar to conventional television display; i.e., the received echo signals are utilized to modulate the brightness of the display at each point scanned. This type of display is found especially useful when the ultrasonic energy is scanned transverse the body so that individual "ranging" information yields individual scan lines on the display, and successive transverse positions are utilized to obtain successive scan lines on the display. This type of technique yields a cross-sectional picture in the plane of the scan, and the resultant display can be viewed directly or recorded photographically or on magnetic tape.

While successes have been achieved in the field of ultrasonic imaging, there are a number of problems which need to be overcome in obtaining high quality ultrasonic images in a convenient, reliable and cost-effective manner. Regarding problems which have been partially overcome, it is known, for example, that ultrasound is almost totally reflected at interfaces with gas. This has led to the use of coupling through a fluid such as water or the use of a direct-contact type of transducer. The latter technique may give rise to problems when attempting to image structures such as arteries which may be only a few millimeters below the skin surface, the contact imaging causing aberrations in the near field of the transducer. Coupling through a fluid offers advantage over direct-contact in this respect, but leads to various design problems and cumbersome generally non-portable structures which have inconvenient to use, especially when attempting to register them accurately on a patient. Some techniques involve immersing the patient in water or obtaining appropriate contact of the body part with a bulky water tank wall.

The need to scan the ultrasonic beam in two dimensions has added to the problems of conciseness and cost-effectiveness. One class of techniques utilizes electronic beam steering wherein a multi-element array is utilized in conjunction with dynamic focusing circuitry employing variable delay elements. This technique is generally complex, especially when used to achieve scanning in two dimensions. Also, at the necessary bandwidths, it is found that the delay elements in such circuitry, including numerous fixed delay elements, become physically cumbersome and add cost, size, and weight to the scanning units.

The above factors, inter alia, contribute to the difficulty in obtaining an ultrasonic imaging apparatus which is convenient to use, portable, relatively cost-effective, and has these attributes without sacrificing necessary operational characteristics. It is among the objects of this invention to provide such an apparatus and to offer solution to prior art problems as set forth.

SUMMARY OF THE INVENTION

The present invention is utilized in an ultrasonic apparatus for imaging sections of a body by transmitting ultrasonic energy into the body and determining the characteristics of the ultrasonic energy reflected therefrom. Such an apparatus typically includes timing means for generating timing signals, energizing/receiving means alternately operative in response to the timing signals, and display/record means, synchronized by the timing signals, for displaying and/or recording image-representative electronic signals from the energizing/receiving means.

In accordance with the invention there is provided a portable scanning module, suitable for being hand held, which comprises fluid-tight enclosure having a scanning window formed of a flexible material. A transducer is provided for converting energy from the energizing/receiving means to periodic ultrasonic energy and for converting reflected ultrasonic energy to electrical signals, the transducer having a plurality of defined segments. A variable delay means is coupled between the segments of the transducer and the energizing/receiving means, the variable delay means being responsive to the timing signals to effect electronic focusing of signals coupled therethrough. A focusing lens is coupled to the transducer. Fluid means, such as water, is contained in the enclosure in the volume between the focusing lens and the scanning window. A reflective scanning means is disposed in the fluid means between the lens and the window, and driving means, synchronized with the timing signals, is provided for moving the scanning means in periodic fashion.

In a preferred embodiment of the invention the focusing lens has a general contour which effects focusing at or from a point in a range of foci, the lens having a number of geometrical steps in its general contour substantially overlaying the positions of at least some of the transducer segments. In this embodiment, the geometrical steps introduce fixed propagation delays as a function of their step height and as a function of the index of refraction of the lens material with respect to the index of refraction of the fluid.

In accordance with a further feature of the invention, the reflective scanning means comprises a supportive surface and a thin sheet of ultrasonically-transmissive material mounted over the surface. A gaseous region is located between the supportive surface and the material. The transmissive material is typically a thin transparent foil and the supportive surface is sufficiently rough such that the material contacts the surface only at a relatively small percentage of its surface area. In this manner, the gaseous region, typically a microscopic layer of air, causes virtually total reflection of the ultrasound regardless of considerations of critical angle at incidence.

Further features and advantages of the invention will become more readily apparent from the following detailed description when taken in conjunction with the accompanying drawings.

BRIEF DESCRIPTION OF THE DRAWINGS

FIG. 1 illustrates the operation of a scanning apparatus which employs the improvements of the invention.

FIG. 5 illustrates an embodiment of the invention wherein a pair of transducers and lenses are utilized in a scanning module to obtain a beam having an even larger total aperture.

FIG. 6 illustrates a portion of a further embodiment of the invention.

DESCRIPTION OF THE PREFERRED EMBODIMENT

Figure 2:
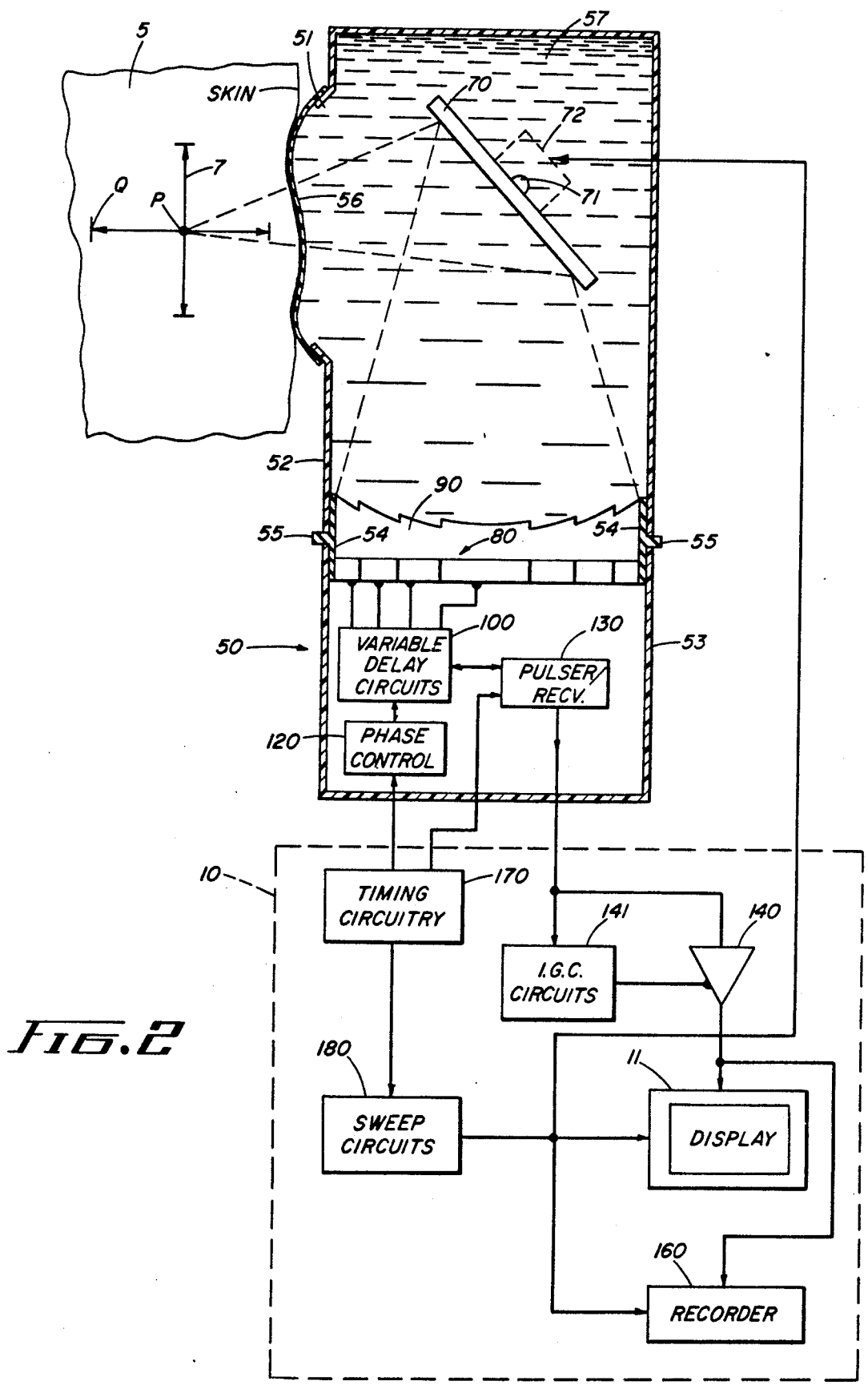
FIG. 2 shows a cross-sectional view of a portion of the scanning module along with diagrams of portions of circuitry therein and in the accompanying console.

Referring to FIG. 1, there is shown an illustration of a scanning apparatus which employs the improvements of the invention. A console 10 is provided with a display 11 which may typically be a cathode ray tube television-type display, and a suitable control panel. A video tape recorder or suitable photographic means may also be included in the console. The console will also typically house power supplies and portions of the timing and processing circuitry of the system, to be described. A portable scanning module or probe 50 is coupled to the console by cable 48. In the present embodiment the probe is generally cylindrical in shape and has a scanning window 51 near one end, the scanning window being defined by protruding flexible material, which may typically be silicone rubber. During operation of the apparatus, the probe 50 is hand held to position the scanning window over a part of the body to be imaged. For example, in FIG. 1 the probe is positioned such that a cross section of the heart will be obtained. Imaging of other portions of the body is readily attained by moving the probe to the desired position and orientation, the relative orientation of the scanning window determining the angle of the cross section taken.

Referring to FIG. 2, there is shown a cross-sectional view of a portion of the scanning module or probe 50 along with diagrams of portions of the circuitry therein and in console 10 used in conjunction therewith. An enclosure, which may be formed of plastic, consists of a front cover 52 which defines the fluid-tight compartment, and a rear cover 53 which houses at least a portion of the system electronics. Both covers are generally cylindrical in shape and fit, with suitable seals, over a cylindrical inner housing 54 having an annular rim 55. The inner housing holds a segmented transducer 80 and a focusing lens 90, to be described. The scanning window 51 is defined by a generally rectangular opening in the side of cover 52, the opening having a slightly protruding lip on which is mounted a flexible material 56, which may be a silicone or neoprene rubber membrane. The volume of the enclosure defined by front cover 52 is filled with a fluid 57, for example water. The membrane 56 will accordingly conform in shape to the surface of a body portion with which it is placed in contact, thereby minimizing the possibility of an undesirable reflective liquid-air interface.

A reflective scanner 70, which is flat in the present embodiment but which may be curved to provide focusing if desired, is disposed in the fluid 57 between the lens 90 and the scanning window 51. The scanner 70 is mounted on a shaft 71 (perpendicular to the plane of the paper) which passes through a suitable seal in cover 52 and is connected to a small electric motor 72 which is mounted on the outside of cover 52 and provides the desired ocsillatory or sawtooth motion. The motor 72, which is shown in dashed line in the FIGURE, may be provided with separate small cover (not shown) which constitutes a protrusion on the cover 52 or an irregular outer shape can be avoided by providing a secondary larger outer shell (not shown).

The segmented transducer 80 is coupled to variable delay circuitry 100 which includes variable delay elements (and may include some fixed delay elements, as will be described hereinbelow) whose values are controlled by phase control circuitry 120. A pulser/receiver circuit 130 alternately provides energizing pulses to and receives echo signals from the segmented transducer 80, both these operations being coupled through the variable delay circuitry 100 which provides dynamic focusing, in known manner. The receiver portion of circuit 130 includes a preamplifier which is coupled through gain control amplifier 140 to display 11 and recorder 160, which may be any suitable recording or memory means, such as a video tape recorder. The gain control circuitry may include interactive gain compensation ("IGC"), which is shown as block 141 and described in detail in copending U.S. application Ser. No. 569,185 filed Apr. 18, 1975, now U.S. Pat. No. 4,043,181 and assigned to the same assignee as the present application. This circuitry compensates the amplitude of later arriving signals for attenuation experienced during passage through body tissue and losses due to prior reflections. Timing circuitry 170 generates timing signals which synchronize operation of the system; the timing signals being coupled to the previously described circuitry and also to sweep circuitry 180 which generates the signals that control the oscillations of scanner 70 and the vertical and horizontal sync signals for the display 11 and recorder 160.

In broad terms, operation of the system is as follows: Upon command from the timing circuits the pulser in circuitry 130 generates pulses which excite the segments of transducer 80 via a portion of the variable delay circuitry 100 (or a second separate set of delay circuitry—not shown) which is, in turn, controlled by phase control circuitry 120. If all segments of the transducer were excited at the same time (i.e., in phase), the ultrasonic energy would be focused approximately at a point determined by the focusing properties of lens 90; e.g. the point P in the body 5 as shown in FIG. 2, with the dashed lines depicting the beam outline. As is known in the art, the depth of focus can be varied electronically by imparting predetermined delays or phase changes to different segments of the transducer 80. When the ultrasound pulse is launched the variable delay circuit is set so that the transmitted beam is focused at the point Q which is the deepest (furthest) point at which the image is being sought.

When the focused beam for a given scanline has been transmitted toward the body, the timing circuitry causes the pulser/receiver 130 to switch into a "receive" or "listen" mode and also activates a reverse cycle of the phase control circuitry 120. Now, the transducer segments serve to convert the received ultrasound energy into electrical signals which are combined in proper phase relationship for focusing on particular reflection origination points in the range of depths being investigated. For example, at an instant of time t after the pulse was transmitted, it is known that the arriving echoes will be coming from a depth of about t/2C (where C is the propagation velocity—assumed, for ease of illustration, to be the same in the body as in the fluid 57). For such echoes the arrival phases at each of the transducer segments can be predetermined. Thus, at a time t the phase control circuitry provides these time delays at each transducer segment. For a "B-scan" display, a sweep over the range of depths corresponds to a horizontal scanline of the display, so the timing signals from circuitry 170 synchronize the horizontal sync of the display with the phase control circuitry 120 providing appropriate delays as the successive echoes arrive from increasing depths until one entire "scan line" is completed, typically from the patient's skin up to a fixed preselected depth in the body. The second dimension of the desired cross-sectional image is attained by a slower mechanical scan of scanner 70 which is synchronized with the vertical sweep rate of the display and recorder by the sweep circuitry 180. The mechanical scanning range is illustrated by the double-headed arrow 7.

The received signals are coupled through the preamplifier in pulser/receiver 130 and through gain control amplifier 140 to display 11 wherein the signals modulate the brightness of the scanning raster to obtain the desired cross-sectional image. The signals are also recorded on the video tape recorder 160.

Figure 3:
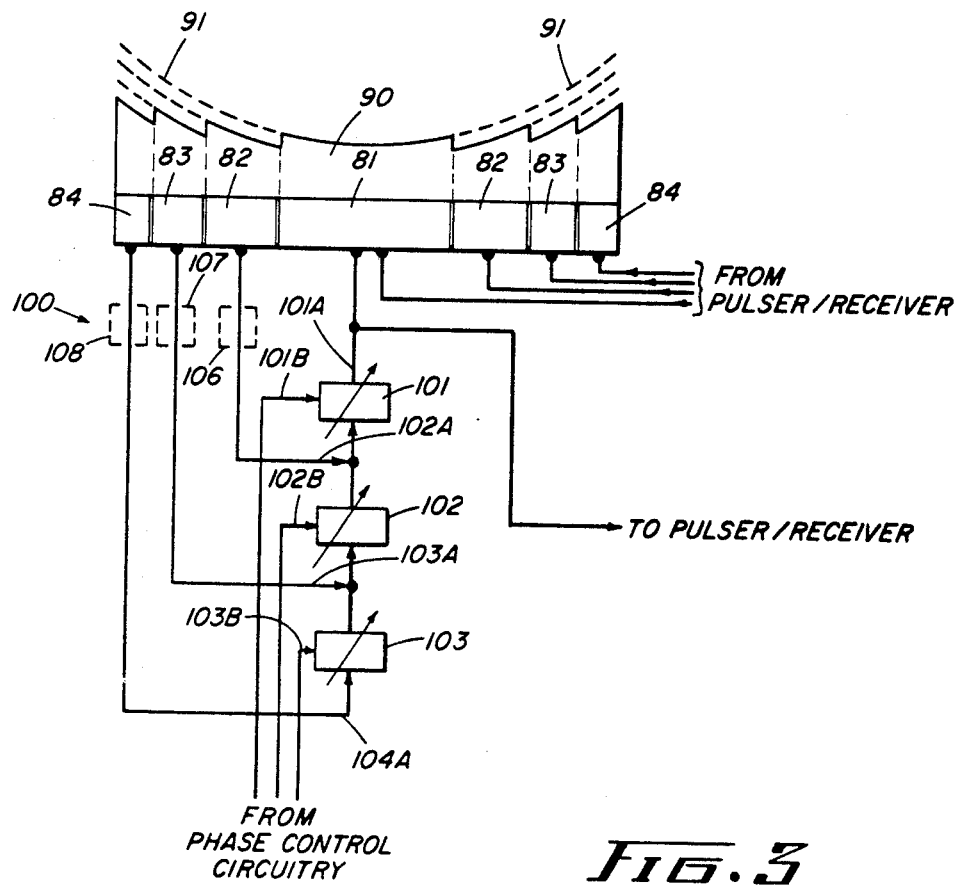
FIG. 3 illustrates, in further detail, the focusing lens 90 shown in FIG. 2, illustrated in conjunction with the segmented transducer and variable delay circuitry.

Referring to FIG. 3, there is illustrated in further detail the focusing lens 90 in accordance with the invention, shown in conjunction with the segmented transducer 80 and a portion of the variable delay circuitry 100, also in further detail. The transducer 80, typically formed of a piezoelectric ceramic, is segmented into a circular center disc 81 and isolated annular rings 82, 83 and 84. Segmented transducers of this form are known in the art and, while only four segments are shown for ease of illustration, it will be appreciated that a larger number of segments can be employed. The lens 90, which preferably has a relatively flat surface opposing the transducer, may be a bonded lens or attached to the transducer using a thin layer of gel. The lens is preferably formed of a plastic material selected in accordance with the principles set forth in co-pending U.S. application Ser. No. 515,352 filed Oct. 16, 1974 now U.S. Pat. No. 3,458,559, assigned to same assignee as the present application. As disclosed therein, by selecting the lens material in accordance with specified parameters, "apodization" is achieved; i.e., undesired output side lobes, caused by factors such as finite transducer size, are minimized. Further, in accordance with the last referenced co-pending U.S. application, the lens 90 has a generally elliptical contour, as depicted by dashed line 91, which provides desired focusing in the manner described in said co-pending application.

The variable delay circuitry 100 includes variable delay units 101, 102 and 103 connected in a series arrangement. Each unit may comprise conventional components for obtaining variable delay including, for example, a varactor diode. The illustrated series arrangement constitutes a multiple-entry analog tapped delay line with lines 101A, 102A, 103A and 104A being coupled from the points shown to metalization electrodes on the respective transducer segments 81, 82, 83 and 84. Lines 101B, 102B and 103B, which originate from phase control circuitry 120, are coupled to the units 101, 102 and 103 and serve to control the amount of delay provided by each unit. The summed output is taken at one end (either at line 101A, as shown in the FIG., or at 104A).

To better understand the nature of this improved feature of the invention, fixed delay units 106, 107 and 108 are shown as being present in the lines 102A, 103A and 104A, respectively, consistent with the output being at 101A. During operation, as previously described, the phase control circuitry 120 generates signals, which appear on the lines 101B, 102B and 103B, these signals causing appropriate variation of the delay units 101, 102 and 103, in known manner, to provide electronic focusing of the beam. In the prior art, the fixed electronic delays 106, 107 and 108, are generally required in conjunction with the illustrated variable delays. The size of these fixed delays will depend on various system parameters, with typical values being in the range of tens of nanoseconds to a few microseconds. At the necessary bandwidth (of typically several megahertz in frequency), these fixed delays involve substantial size and cost, especially where a relatively large number of transducer segments are utilized. In the present invention, as seen in the FIGURE, the need for some or all of the fixed electronic delays is eliminated by introducing appropriate ultrasonic wave propagation delays which are achieved by providing discrete geometrical steps in the general contour of the lens. Each step overlays the position of one of the transducer segments and produces a delay which depends on the step height and the index of refraction of the lens material with respect to the propagation medium. Stated another way, since the velocity of ultrasound in the propagating fluid 57 (water, in this case), is less than the velocity of ultrasound in the lens material (plastic, in this case), delay is introduced by causing the ultrasonic energy to travel further in the slower medium. Of course, depending on the choice of lens material and propagating medium utilized, as well as whether "positive" or effective "negative" delay is desired, the steps in the lens can rise toward the center (as shown) thereof or toward the outer edge. In FIG. 3 the transducer segments 82, 83 and 84 respectively have one, two and three units of delay associated with them. For a particular design configuration, each unit step was calculated as providing 150 nanoseconds of delay, so the "fixed" delays associated with the lines 106, 107 and 108 for this case would be 150 ns., 300 ns. and 450 ns., respectively.

Figure 4:
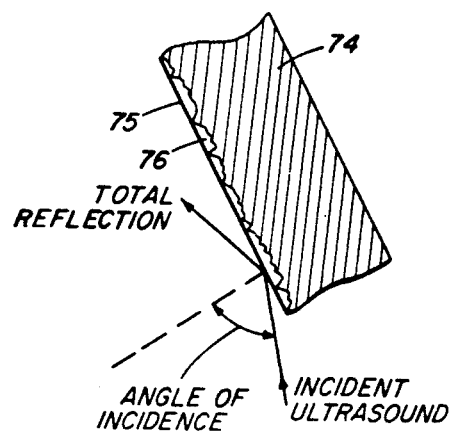
FIG. 4 shows a microscopic view of a portion of the reflective scanner of FIG. 2.

Referring to FIG. 4, there is shown a microscopic view of a portion of the surface of the reflective scanner 70 of FIG. 2. The scanner is designed in a way which insures total reflection of the ultrasound energy, notwithstanding whether or not the angle of incidence of such energy is beyond the critical angle for total reflection. Typically, where a reflective coating is utilized, a problem can arise when "dual" or "multiple" reflection occurs from both the outer surface of the reflective coating and the interface between the inner surface thereof and its substrate; the problem being manifested by resultant multiple transmit pulses. One way to avoid this is to design the equipment such that the ultrasound is incident on the reflector at an angle greater than the critical angle whereby all the sound energy gets reflected from the front surface of the reflector and no sound energy goes into the reflector to cause secondary reflections. It is desirable to not be constrained to incidence angles greater than the critical angle, especially since the ultrasound beam has a substantial range of incidence angles over the reflector surface, and the angle is constantly changing at any particular point thereon as the reflector is scanned. Accordingly, applicant provides a reflector which makes use of the total reflection of ultrasound at a liquid/gas interface.

In the present embodiment the reflector comprises a flat piece of substrate material 74, typically a metal such as steel having a finish which is not optically polished and has a roughness which is, for example, of the order of one to ten microns. An exceedingly thin layer of ultrasonically transparent material 75, such as a plastic foil having a thickness of about 1-2 mils (much smaller than the wavelength of the ultrasound), overlays the substrate. As can be seen from the microscopic view, during fabrication of the reflector a thin layer of air 76 is trapped in the asperities on the surface of the substrate 74; i.e., between the substrate surface and the layer 75. Applicant has discovered that the incident ultrasound is completely reflected at what operates effectively as a liquid/air interface, so that considerations of critical angle are obviated.

Referring to FIG. 5, there is shown an embodiment of the invention wherein a plurality of segmented transducer/lens combinations, 80A and 90A, as well as the previously described 80 and 90, are utilized to obtain a larger total aperture ultrasound beam. The additional combination may be mounted parallel to the elements 80 and 90 (as shown), or at an angle thereto. The accompanying circuitry for each combination can be essentially the same as shown in FIG. 2, with provision being made for integrating the scanning beams. The beams are directed toward the reflective scanners 70 and 70A, as shown, and operation is generally the same as that described in conjunction with FIG. 2. A single scanner could also be employed.

Referring to FIG. 6, there is shown a portion of an embodiment of the invention wherein a separate transducer designated 80B is utilized to transmit the ultrasound beam from the position of the reflector 70. This technique is applicable when electronic variable focusing is provided in only the "receive" or "listening" mode, as is generally the case. A coupling medium 95 couples the transducer to the reflector, and energizing signals from the pulser/receiver (see e.g. FIG. 3) are coupled to the transducer 80B. In other respects, the system is similar to the embodiment shown in FIG. 2, with the lens 90 and transducer 80 (and associated circuitry) processing reflected echoes as previously described. The transmitting transducer 80B, which moves with the reflector 70, scans one scan line at a time and echoes are reflected toward the receiving transducer 80, as shown by the dashed lines and arrows. In this embodiment, the total ultrasound travel path is smaller so that successive pulses (for each scan line) can be transmitted at a higher rate with an accompanying desirable increase in the overall imaging rate.

The invention has been described with reference to particular embodiments, but variations within the spirit and scope of the invention will occur to those skilled in the art. For example, some or all of the timing or sweep circuitry of FIG. 2 may be housed in the scanning module 50, if desired, the basic consideration being the desire to maintain portability of the module while still minimizing the noise-susceptibility of low-level signals passing through cables between the scanning module and the console. Also, it will be understood that transmit focusing could be used, if desired. Finally, it can be noted that the present invention is particularly applicable to ultrasonic surgery techniques wherein, after imaging and observing a diseased tissue such as a tumor growth, it is desired to "eliminate" diseased tissue by exposing it to very high intensity ultrasound. In such a case, after the imaging sequence, the scanner can be electrically aligned with the tumor and the transmitted power of the transducer increased, such as by a factor of 10,000. The phase coding circuitry is controlled so that the high power beam is focused only at the tumor site and defocused at other sites so that thermal damage of healthy tissue does not occur. The equipment can be periodically switched back to the imaging mode so as to monitor the effects of treatment during the surgery.

I claim:

1. In an ultrasonic apparatus for imaging sections of a body by transmitting ultrasonic energy into the body and determining the characteristics of the ultrasonic energy echoing therefrom, said apparatus including timing means for generating timing signals; energizing/receiving means operative in response to the timing signals; and display/record means synchronized with said timing signals for displaying and/or recording image-representative signals from the energizing/receiving means; a scanning module, comprising:

a fluid-tight enclosure having a scanning window;
a fluid contained in said enclosure;
a reflective scanner disposed in said fluid;
a first transducer, mounted in conjunction with said reflective scanner, for converting energy from said energizing/receiving means to ultrasonic energy;
a second transducer spaced from said scanning window and said reflective scanner for converting ultrasonic echoes reflected from said reflective scanner to electrical signals, said electrical signals being coupled to said energizing/receiving means; and
driving means synchronized with said timing signals for moving said reflective scanner in periodic fashion.

2. The scanning module as defined by claim 1 further comprising a focusing lens coupled to said second transducer.

3. The scanning module as defined by claim 2 wherein said second transducer is segmented and wherein said focusing lens has a number of geometrical steps substantially overlaying the positions of at least some of the segments of said second transducer, whereby said geometrical steps introduce fixed propagation delays as a function of their step height and the index of refraction of the lens material with respect to the index of refraction of said fluid.

4. The scanning module as defined by claim 3 wherein said lens is substantially flat on its side opposing said second transducer and has said geometrical steps in its general contour.

5. The scanning module as defined by claim 1 wherein said reflective scanner comprises a supportive surface; a thin sheet of ultrasonically-transmissive material mounted over said surface; and a gaseous region located between said supportive surface and said material.

6. The scanning module as defined by claim 5 wherein said supportive surface is sufficiently rough that said material contacts said surface at a relatively very small percentage of its surface area.

7. The scanning module as defined by claim 6 wherein said gaseous region contains air.

* * * * *